(12) United States Patent
Amoah et al.

(10) Patent No.: US 10,426,542 B2
(45) Date of Patent: Oct. 1, 2019

(54) ELECTROSURGICAL APPARATUS HAVING RF PULSE PROFILE CONTROLLER

(71) Applicant: CREO MEDICAL LIMITED, Chepstow, Monmouthshire (GB)

(72) Inventors: Francis Amoah, Chepstow (GB); Christopher Paul Hancock, Chepstow (GB); Martin Jarman, Chepstow (GB); Nuwan Dharmisiri, Chepstow (GB)

(73) Assignee: CREO MEDICAL LIMITED, Chepstow (GB)

(*) Notice: Subject to any disclaimer, the term of this patent is extended or adjusted under 35 U.S.C. 154(b) by 860 days.

(21) Appl. No.: 14/889,795

(22) PCT Filed: Apr. 14, 2014

(86) PCT No.: PCT/GB2014/051165
§ 371 (c)(1),
(2) Date: Nov. 6, 2015

(87) PCT Pub. No.: WO2014/181078
PCT Pub. Date: Nov. 13, 2014

(65) Prior Publication Data
US 2016/0120588 A1    May 5, 2016

(30) Foreign Application Priority Data
May 8, 2013    (GB) .................................. 1308207.8

(51) Int. Cl.
*A61B 18/12*    (2006.01)
*A61B 18/18*    (2006.01)
(Continued)

(52) U.S. Cl.
CPC ...... *A61B 18/1206* (2013.01); *A61B 18/1815* (2013.01); *A61B 18/1402* (2013.01);
(Continued)

(58) Field of Classification Search
CPC .......... A61B 2018/00636; A61B 2018/00702; A61B 2018/00648; A61B 2018/00726;
(Continued)

(56) References Cited

U.S. PATENT DOCUMENTS 5,715,832 A * 2/1998 Koblish ................. A61B 10/06
600/564
2002/0099368 A1* 7/2002 Schulze ............. A61B 18/1445
606/45

(Continued)

FOREIGN PATENT DOCUMENTS

EP    1 658 817 A1    5/2006
GB    2 486 343 A     6/2012
(Continued)

OTHER PUBLICATIONS

International Search Report and Written Opinion of PCT/GB2014/051165.
(Continued)

*Primary Examiner* — Ronald Hupczey, Jr.
(74) *Attorney, Agent, or Firm* — Arent Fox LLP

(57) ABSTRACT

A pulsed RF cut waveform profile for electrosurgery, in which each pulse is formed of a composite of different pulse portions. The pulse includes a controllable treatment portion whose duration can be truncated as necessary to ensure that the average power delivered by the pulse as a whole does not exceed a predetermined value. A limit for the average power delivered by the composite pulse (i.e. total energy delivered over the duration of the ON and OFF portions divided by the pulse duration) may be selectable by the operator. The ON portion may have multiple sub-portions, which have different purposes. Each pulse may be automatically controlled
(Continued)

for pulse width in this manner, so that the RF signal effectively responds intelligently to conditions at the probe tip during treatment.

25 Claims, 6 Drawing Sheets

(51) Int. Cl.
*A61B 18/14* (2006.01)
*A61B 18/00* (2006.01)

(52) U.S. Cl.
CPC ............ *A61B 2018/00601* (2013.01); *A61B 2018/00702* (2013.01); *A61B 2018/00726* (2013.01); *A61B 2018/00779* (2013.01); *A61B 2018/00785* (2013.01); *A61B 2018/00827* (2013.01); *A61B 2018/00875* (2013.01); *A61B 2018/00892* (2013.01); *A61B 2018/00994* (2013.01); *A61B 2018/1412* (2013.01); *A61B 2018/1823* (2013.01)

(58) Field of Classification Search
CPC .......... A61B 2018/00779; A61B 2018/00785; A61B 2018/00875; A61B 2018/00827; A61B 2018/00892
See application file for complete search history.

(56) References Cited

U.S. PATENT DOCUMENTS

| | | |
|---|---|---|
| 2003/0139741 A1 | 7/2003 | Goble et al. |
| 2007/0167941 A1 | 7/2007 | Hamel et al. |
| 2010/0049187 A1* | 2/2010 | Carlton ................ A61B 5/0059 606/34 |
| 2010/0241116 A1 | 9/2010 | Fenamou et al. |
| 2011/0270265 A1* | 11/2011 | Fleming ............... A61B 17/295 606/114 |
| 2012/0022519 A1 | 1/2012 | Huang et al. |
| 2012/0265196 A1* | 10/2012 | Turner ........... A61B 17/320092 606/34 |

FOREIGN PATENT DOCUMENTS

| | | |
|---|---|---|
| JP | 2004-512135 A | 4/2004 |
| WO | WO 2008/102154 A2 | 8/2008 |
| WO | WO 2012/076844 A1 | 6/2012 |
| WO | WO 2012/095653 A1 | 7/2012 |

OTHER PUBLICATIONS

British Search Report of related British Patent Application No. GB1308207.8 dated Nov. 12, 2013.
Japanese Office Action of related Japanese Patent Application No. 2016-512410 dated Feb. 27, 2018.

* cited by examiner

ELECTROSURGICAL APPARATUS HAVING RF PULSE PROFILE CONTROLLER

CROSS-REFERENCE TO RELATED APPLICATION

This application is a National Stage entry of International Application No. PCT/GB2014/051165, filed Apr. 14, 2014, which claims priority to United Kingdom Patent Application No. 1308207.8, filed May 8, 2013. The disclosures of the priority applications are incorporated in their entirety herein by reference.

TECHNICAL FIELD

The invention relates to electrosurgical apparatus in which radiofrequency energy is used to treat biological tissue. In particular, the invention relates to surgical apparatus capable of generating radiofrequency (RF) energy for cutting tissue, It may be used in as part of a surgical apparatus which also delivers microwave frequency energy for haemostasis (i.e. sealing broken blood vessels by promoting blood coagulation).

BACKGROUND TO THE INVENTION

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting. For endoscopic procedures, it is also undesirable for a bleed to occur and not to be dealt with as soon as quickly as possible, or in an expedient manner, since the blood flow may obscure the operator's vision, which may lead to the procedure needing to be terminated and another method used instead, e.g. open surgery.

Electrosurgical generators are pervasive throughout hospital operating theatres, for use in open and laparoscopic procedures, and are also increasingly present in endoscopy suites. In endoscopic procedures the electrosurgical accessory is typically inserted through a lumen inside an endoscope. Considered against the equivalent access channel for laparoscopic surgery, such a lumen is comparatively narrow in bore and greater in length. In the case of a bariatric patient the surgical accessory may have a length of 300 mm from handle to RF tip, whereas the equivalent distance in a laparoscopic case can be in excess of 2500 mm.

Instead of a sharp blade, it is known to use radiofrequency (RF) energy to cut biological tissue. The method of cutting using RF energy operates using the principle that as an electric current passes through a tissue matrix (aided by the ionic contents of the cells and the intercellular electrolytes), the impedance to the flow of electrons across the tissue generates heat. When an RF voltage is applied to the tissue matrix, enough heat is generated within the cells to vaporise the water content of the tissue. As a result of this increasing desiccation, particularly adjacent to the RF emitting region of the instrument (referred to herein as an RF blade) which has the highest current density of the entire current path through tissue, the tissue adjacent to the cut pole of the RF blade loses direct contact with the blade. The applied voltage is then appears almost entirely across this void which ionises as a result, forming a plasma, which has a very high volume resistivity compared to tissue. This differentiation is important as it focusses the applied energy to the plasma that completed the electrical circuit between the cut pole of the RF blade and the tissue. Any volatile material entering the plasma slowly enough is vaporised and the perception is therefore of a tissue dissecting plasma.

GB 2 486 343 discloses a control system for an electrosurgical apparatus which delivers both RF and microwave energy to treat biological tissue. The energy delivery profile of both RF energy and microwave energy delivered to a probe is set based on sampled voltage and current information of RF energy conveyed to the probe and sampled forward and reflected power information for the microwave energy conveyed to and from the probe.

SUMMARY OF THE INVENTION

The present invention provides an enhancement to the electrosurgical apparatus disclosed in GB 2 486 343. The enhancement concerns the waveform of the RF signal used for tissue cutting, and in particular may ameliorate the impact of an increased cable length on the accuracy of control of RF waveforms delivered to the tip of the probe.

At its most general, the present invention provides a pulsed RF cut waveform profile in which each pulse has a controllable treatment portion whose duration can be truncated as necessary to ensure that the average power delivered by the pulse as a whole does not exceed a predetermined value. A limit for the average power delivered by the composite pulse (i.e. total energy delivered over the duration of the ON and OFF portions divided by the pulse duration) may be selectable by the operator. The ON portion may have multiple sub-portions, which have different purposes. Each pulse may be automatically controlled for pulse width in this manner, so that the RF signal effectively responds intelligently to conditions at the probe tip during treatment.

Thus, according to one aspect of the invention, there may be provided electrosurgical apparatus for resection of biological tissue, the apparatus comprising: a radiofrequency (RF) signal generator for generating an RF waveform having a first frequency; a probe arranged to deliver the RF waveform from a distal end thereof; a feed structure for conveying the RF waveform to the probe along an RF channel; an RF signal detector for sampling current and voltage on the RF channel and generating therefrom a RF detection signal indicative of the current and voltage; and a controller in communication with the RF signal detector to receive the RF detection signal, wherein the RF signal generator is arranged to deliver the RF waveform as a plurality of RF signal pulses, each of the plurality of RF signal pulses having a predetermined power limit and a pulse duration, wherein the controller is arranged to: monitor, based on the RF detection signal, energy accumulated in the biological tissue during the pulse duration of each of the plurality of RF signal pulses, and control the profile of each of the plurality of RF signal pulses to keep an average power delivered by that RF signal pulse to the biological tissue over its respective pulse duration below a target value. The target value for the average power is preferably substantially lower than the predetermined power limit for the RF signal pulse, e.g. less than 50% thereof, preferably in the range 15-50% thereof, more preferably in the range 20-30% thereof. This arrangement of energy delivery provides two main advantages. Firstly, it enables a high peak power, useful for initiating cutting action, to be used without undesirably increasing the total energy delivered into the biological tissue. Secondly, it enables a pulsed waveform to dynamically adapt to the treatment conditions to ensure that energy is delivered efficiently without causing arcing or other unwanted artifacts at the probe tip.

For the purpose of bipolar electrosurgical dissection, the basic waveform generated by the RF signal generator may be a sine waveform of greater than 260 Vrms at a radio frequency of between 100 kHz and 5 MHz.

The controller may comprise a digital microprocessor (e.g. microcontroller) programmed to output an RF control signal for the RF signal generator, wherein the profile of the cut initiation portion and/or cut sustain portion of each RF signal pulse is controlled based on a state of the RF control signal. Herein "profile" may mean the shape, e.g. any one or more of the duration, amplitude, and waveform, of the relevant portion of the RF signal pulse. In practice, this control may be achieved by setting limits on the voltage and current delivered to the probe. Preferably, the controller is arranged to control the duration of the ON portion of each of the plurality of RF signal pulses to keep an average power delivered by that RF signal pulse to the biological tissue over its respective pulse duration below a target value.

The controller may be arranged to cause each of the plurality of RF signal pulses to include: a cut initiation portion during which the controller sets a cut initiation voltage limit for the respective RF signal pulse, and a cut sustain portion during which the controller sets a cut sustain voltage limit for the respective RF signal pulse, wherein the cut sustain voltage limit is less than the cut initiation voltage limit, and the cut sustain portion follows the cut initiation portion. Preferably, the cut initiation portion is uniform in each RF signal pulse, i.e. with a fixed duration (e.g. 20 ms or less). Thus, the average power of the pulse across its duration may be determined solely by controlling the profile of the cut sustain portion. In practice, this may be done by assigning a constant sustain voltage limit and varying the duration of the cut sustain portion. The power level depends on the current and voltage delivered on the RF channel. In one embodiment, the voltage limit does not change within each of the cut initiation portion and the cut sustain portions; the power level is controlled by adjusting the current, for a given impedance at the load end of the RF channel. Thus, the controller may be arranged to control the duration of the cut sustain portion to cause an average power delivered by that RF signal pulse to the biological tissue over its respective pulse duration to meet a target value.

In one embodiment, the RF control signal is a demand signal for a pulse width modulator (PWM) integrated circuit (IC). The PWM IC controls an input signal to the RF signal generator (e.g. a DC input to a RF inverter), and hence influences the RF waveform generated by the RF signal generator.

The state of the RF control signal may be determined by a control loop, which runs repeatedly throughout the pulse duration of each RF signal pulse. The faster the control loop runs, the quicker the signal can adapt to the treatment conditions. The control loop period may be 10 ms or less, preferably 100 μs or less. The fixed duration of the cut initiation portion may correspond to a predetermined number of control loop periods. The control loop may function to adaptively set limiting values for the voltage and current delivered to the probe.

Each pulse duration may include an OFF portion in which no power is delivered, the OFF portion being between the cut sustain portion of its respective pulse and the cut initiation portion of the next pulse. The pulse duration for each of the plurality of RF signal pulses is preferably constant, which means that duration of the OFF portion may vary in a complementary manner with the duration of the cut sustain portion. Preferably, the control loop is arranged to ensure that the OFF portion can have a minimum duration. Each pulse duration may also include a short information acquisition portion (e.g. to detect the impedance of the load at the distal end of the probe) before the cut initiation portion. During the acquisition portion the controller may be arranged set s current or voltage limit that would prevent the predetermined power, voltage and current limits being exceeded, in the absence of any tissue impedance data, e.g. a voltage limit $V_{limit}$ may be set as $P_{limit}/I_{limit}$, where $P_{limit}$ and $I_{limit}$ are the power and current limits respectively from the three parameter load curve associated with the apparatus configuration. In a preferred embodiment, a voltage limit from the acquisition portion is set to be the same as the cut initiation voltage limit, and the current limit is set to a value for an unloaded cable or for the intersection between the power limit boundary and the voltage limit boundary of the three parameter load curve. As explained below, setting the current limit may comprise determining a target current and computing from a value for the current limit at the generator by considering a lumped shunt capacitance associated with the RF channel. In this case, the target current may be calculated as $I_t = P_{pk}V_{ini}$, where $P_{pk}$ is the intra pulse power limit and $V_{ini}$ is the cut initialisation voltage limit. Controlling the voltage limit in the absence of tissue impedance data to assure the power limit is not exceeded is almost certain to result in a non-cutting data acquisition portion, whereas controlling the current limit to assure the power limit is not exceeded in the absence of tissue impedance data tends to result in a non-cutting data acquisition portion predominantly when the tissue impedance is low and is more likely to result in an early pulse length termination based on macroscopic average power limiting. The current limit control paradigm may therefore be likely to be less obstructive to cutting, in the more prevalent scenario of cutting with light tissue contact.

Thus, in practice, the controller may be arranged to stop the cut sustain portion (i.e. switch the delivered power to zero if the monitored accumulated energy exceeds a predetermined threshold. The accumulated energy may be determined by obtaining one or more measurements of voltage and current on the RF channel in each control loop period in order to determine an amount of energy delivered during that control loop period. The accumulated energy over N measurements (i.e. data acquisition points) may be expressed as $\Sigma_{n=1}^{N} V_n I_n \tau$, where $V_n$ is the measured voltage of the nth data acquisition point, $I_n$ is the measured current of the nth data acquisition point, and τ is the duration between each data acquisition point (assumed here to be constant). Measurements may be taken every 10-20 μs, for example. The predetermined threshold for the accumulated energy may be programmed into the device, and may be associated with an average power to be delivered by a notional static pulse profile. For example, it is known that RF cutting can be performed satisfactorily by a pulsed signal having a duty cycle of 71% with an average power of 30 W. For a pulse duration of 140 ms, this equates to an energy shot of 4.2 J per pulse, which may be used as the predetermined threshold or target. If the accumulated energy exceeds the threshold, the state of the RF control signal may cause the RF signal pulse to switch to the OFF portion until the start of the next pulse. However, if the OFF portion is to have a minimum duration, the control loop may be arranged to terminate the cut sustain portion if the ON portion duration (i.e. the total duration of the cut initiation and cut sustain portions) exceeds a threshold, even if the accumulated energy is less than the target.

As mentioned above, the predetermined power limit for each RF signal pulse may more than three times greater than the target value for the average power. For example, the predetermined power limit may be 100 W while the target value for the composite pulse average power may be 35 W or less, preferably 30 W or less. The cut initiation voltage limit may be set higher than the cut sustain voltage limit to encourage peak power to be delivered into tissue during the cut initiation portion of the pulse. The cut initiation voltage limit may be 300 Vrms or more. The cut sustain voltage limit may be 290 Vrms or less.

The method of controlling the RF power delivered into tissue set out above may be expressed as a method of controlling radiofrequency (RF) power delivered from a bipolar electrosurgical instrument into a biological tissue at the distal end of the electrosurgical instrument, the method comprising: generating an RF waveform; delivering the RF waveform along an RF channel to the electrosurgical instrument; controlling the profile of the RF waveform by: setting a maximum voltage limit for a voltage applied across the bipolar electrosurgical instrument; sampling current and voltage on the RF channel; and calculating a tissue resistance from the sampled current and voltage, the calculating step including a correction for an impedance associated with the RF channel; determining an objective tissue current limit from the calculated tissue resistance and a predetermined power dissipation target; and dynamically adjusting the current limit based on the determined objective tissue current limit.

The RF waveform may comprise a plurality of RF signal pulses; each RF signal pulse may have a profile controlled as set out above. Where the RF waveform is pulsed the predetermined power dissipation target may be 30% or less of the maximum power limit, as discussed in the first aspect of the invention above. When adjusting the current limit, the method may take account of stray capacitances and feed cable capacitance associated with the RF channel. Such capacitances may be quantified and treated as a lumped element capacitance connected in shunt to the RF channel. The method may thus comprise calculating the maximum current limit $I_{limit}$ as $$I_{limit} = \sqrt{(V_{out}/X_c)^2 + I_t^2},$$

where $V_{out}$ is the sampled voltage, $I_t$ is the objective tissue current, and $X_c$ represents a lumped shunt capacitance associated with the RF channel.

The RF channel may have a length of 3 m or more, e.g. to be capable of delivering RF to an endoscopic probe.

Preferably, the RF waveform has a frequency in the range 100 kHz to 5 MHz, more preferably 300 kHz to 600 kHz.

The steps of the control method above may be executed by a suitably programmed microprocessor, e.g. having an RF control interval in the range 50 µs to 20 ms, more preferably in the range 100 µs to 2 ms.

In addition to cutting, the electrosurgical apparatus of the invention may also be capable of coagulating tissue using microwave frequency energy. The apparatus may thus include a microwave signal generator for generating microwave frequency energy having a second frequency that is higher than the first frequency, wherein the feed structure comprises an RF channel for connecting the probe to the RF signal generator, and a microwave channel for connecting the probe to the microwave signal generator, and wherein the RF channel and microwave channel comprise physically separate signal pathways from the RF signal generator and microwave signal generator respectively, to enable the RF waveform and microwave frequency energy to be selectively delivered simultaneously or separately to the probe.

The apparatus may further include microwave signal detectors for respectively sampling forward and reflected power on the microwave channel and generating therefrom a microwave detection signal indicative of the microwave power delivered by the probe, wherein the controller is in communication with the microwave signal detectors to receive the microwave detection signal, and is arranged to output a microwave control signal for the microwave signal generator, wherein the profile of the microwave frequency energy delivered by the microwave generator is controllable based on a state of the microwave control signal. The controller may be adapted to take account of attenuation between the probe and the microwave signal generator when determining the state for the microwave control signal. In practice, this means that the power of microwave frequency energy delivered into tissue can be controlled. In one embodiment, the apparatus is arranged to deliver an average power of 8 W of microwave energy into biological tissue.

The probe may comprise an electrosurgical resection instrument for applying to biological tissue the RF EM energy, the instrument comprising: an instrument tip comprising a planar body made of a first dielectric material separating a first conductive element on a first surface thereof from a second conductive element on a second surface thereof, the second surface facing in the opposite direction to the first surface; a coaxial feed cable comprising an inner conductor, an outer conductor coaxial with the inner conductor and a second dielectric material separating the inner and outer conductors, the coaxial feed cable being connected to the feed structure for conveying the RF waveform to the instrument tip; and a protective hull comprising a third piece of dielectric material mounted to cover the underside of the instrument tip, wherein the inner conductor is electrically connected to the first conductive element and the outer conductor is electrically connected to the second cutting element to enable the instrument tip to receive the RF waveform, wherein the first and second conductive elements are arranged to act as active and return electrodes to conduct the RF waveform to tissue from a distal or side portion of the planar body, and wherein the protective hull has a smoothly contoured convex undersurface facing away from the planar body.

The first and second conductive elements may be arranged to provide a local return path for RF energy, i.e. a low impedance route for RF energy to be transported between the first and second conductive elements and the tissue. The first and second conductive elements may be layers of metallisation formed on opposite surfaces of the first dielectric material. The first and second conductive elements may be arranged to set up a local electric field at a contact region in which the instrument tip makes contact with the biological tissue. The local electric field can be extremely high, which when present across a lossy conductive medium may cause a microplasma (i.e. a hot thermal plasma) to be formed at the distal or side portions of the planar body, e.g. where contact is made with the biological tissue. The microplasma may be desirable in terms of achieving efficient cutting. The first and second conductive elements may include portions, e.g. plated regions at and adjacent the distal side portion, made from conductive material having a high melting point, e.g. 1500° C. or more, such as titanium, tungsten or the like. Using such materials may prevent the high temperatures of the microplasma from eroding the first and second conductive elements. The first and second conductive elements may also include connecting portions made from conductive materials having lower melting points (e.g. silver, gold and the like) deposited or plated on the higher melting point conductors. The connecting portions may facilitate connection of the inner and outer conductors of the coaxial cable, e.g. by soldering or the like. In one arrangement, a titanium tungsten (TiW) seed layer may be used with a layer of silver (Ag) or gold (Au) deposited on the top. The lower melting point material may be deposited onto the higher melting point material only in the region where the coaxial cable inner and outer conductors are to be attached, i.e. at the proximal end of the instrument only, and not along the sides thereof, where the microplasma will be generated.

The layers of metallisation may be formed from biocompatible materials, e.g. any of silver, titanium and gold. Table 1 below gives the melting and boiling points for materials considered for this device:

TABLE 1

Melting and Boiling Points for conductive materials suitable for use on the instrument tip

| Material | Melting Point (° C.) | Boiling Point (° C.) |
| --- | --- | --- |
| Tungsten (W) | 3422 | 5555 |
| Titanium (Ti) | 1668 | 3287 |
| Silver (Ag) | 961.78 | 2162 |
| Gold (Au) | 1064.18 | 2856 |

Cutting can occur at any edge of the planar structure where there is good, direct contact between both conductors and tissue. Simultaneous good contact between both conductors is more likely if the separation between conductors is small. The plasma is more likely to form at the conductor with the poorer contact with tissue as this tissue tends to desiccate sooner. Once a plasma has formed at one conductor there is a hysteretic effect arising from the dramatic increase in local impedance which tends to avoid the location of the plasma switching back and forth within one continuous application of an RF waveform.

The undersurface of the protective hull may smoothly taper at its perimeter to meet the side of the planar body. The thickness of the protective hull may also decrease towards the distal end of the instrument tip. Thus, the outer portion of the protective hull may have a convex profile. The undersurface may have a longitudinally extending recessed channel formed therein. The tapering edge profile and recessed channel may cause the undersurface of the protective hull to comprise a pair of ridges. This shape may reduce the risk of the instrument digging into the bowel wall and causing a bowel perforation or may protect the portal vein or pancreatic duct from being damaged. The particular dimensions of the hull (e.g. length, width, thickness, etc.) may be adapted to suit the intended use and intended area of the body to be operated on.

The protective hull may be formed from a biocompatible non-conductive material, such as ceramic or biocompatible plastic that does not stick to the wall of the bowel (or other biological tissue) or the like. Alternatively, the hull may also be formed from a metallic material, e.g. titanium, steel, or may be a multi-layer structure. It may be attached (e.g. bonded) to whichever one of the first or second conductive elements is on the underside of the first dielectric material. However, in one arrangement, the protective hull may be formed of the same material as the first dielectric material.

The protective hull and first dielectric material may be formed in one piece as a unitary body. In this arrangement one or more planar slots may be formed (e.g. cut) in the unitary body to allow a conductive material to be inserted to form the first and/or second conductive material.

The instrument tip may be curved at its distal end between the side edges of the planar body. The curve may describe a parabola in the plane of the planar body. The distal end of the protective hull may be curved in a similar manner. This shape prevents the instrument tip from presenting sharp corners to the biological tissue. This shape may also enable cutting to be performed in a direction diagonal to the long axis of the device, in addition to cutting in the same direction or in a direction perpendicular to the long axis.

The instrument may include a fluid feed conduit for delivering fluid (e.g. saline) to the instrument tip. The fluid feed conduit may comprise a passageway through the protective hull for delivering fluid to the treatment site. The passageway may include an outlet located in the recessed channel of the protective hull. The fluid (liquid or gas) may be conveyed to the instrument (protective hull) through a corresponding passageway formed within the coaxial feed cable. The fluid feed conduit may also be used to deliver other material to the treatment site, e.g. a gas or a solid (e.g. powder). In one arrangement, injection of fluid (saline or the like) is used to plump up the biological tissue at the treatment site. This may be particularly useful where the instrument is used to treat the wall of the bowel or the wall of the oesophagus or for protecting the portal vein or the pancreatic duct when a tumour or other abnormality located in close proximity, in order to protect these structures and create a cushion of fluid. Plumping up the tissue in this manner may help to reduce the risk of bowel perforation, damage to the wall of the oesophagus or leakage of from the pancreatic duct or damage to the portal vein, etc.

It is advantageous to be able to use the same instrument to deliver fluid as delivers RF and/or microwave energy since deflation (e.g. due to fluid seepage caused by delay) may occur if a separate instrument is introduced into the region or during treatment. The ability to introduce fluid using the same treatment structure enables the level to be topped up as soon as deflation occurs. Moreover, the use of a single instrument to perform desiccation or dissection as well as to introduce fluid also reduces the time taken to perform the overall polyp removal procedure, reduces the risk of causing harm to the patient and also reduces the risk of infection. More generally, injection of fluid may be used to flush the treatment region, e.g. to remove waste products or removed tissue to provide better visibility when treating. As mentioned above, this may be particularly useful in endoscopic procedures.

The fluid feed conduit may include a needle (e.g. hypodermic needle) mounted beneath the planar body in the recessed channel of the protective hull. The protective hull may include a guide passage for receiving the fluid feed conduit. The needle may have an outer diameter less than 0.6 mm, e.g. 0.4 mm. The needle may be movable in the longitudinal direction between a deployed position in which it protrudes beyond the distal end of the instrument tip and a retracted position in which it is set back from the distal edge of the instrument tip, e.g. below the planar body or locates proximal to the planar body. The needle may be open to fluid flow at the proximal end or side of the needle and may be moved using one or more control wires. For example, the proximal end of needle may be open to the passageway formed within the coaxial feed cable. The needle may be mounted in a through hole formed in the protective hull. The needle may be formed an slidable interference fit with the through hole, where it plugs the through hole to create a fluid path of least resistance through the needle when it is in the deployed position. This arrangement may prevent leaks from other parts of the instrument tip. The through hole may be formed by a tube or similar close-fit bearing surface mounted or formed at the underside of the protective hull, e.g. in the recessed channel.

The instrument may include a sleeve for conveying the coaxial cable, fluid feed conduit (if present) and control wire(s) (if present) to the instrument tip body. The instrument tip body and protective hull may be secured (e.g. bonded) into a distal end of the sleeve. The sleeve may include longitudinal braids to assist in the transfer of torque from its proximal end to the instrument tip. In one arrangement, the braided cable may be made from Pebax® material, and may comprise a plastic outer jacket with a metal braid attached at or to its inner wall. This type of sleeve may provide useful torque stability, whereby a twisting force applied to a handle attached to a proximal portion of the outer jacket of the sleeve is transformed accurately to a rotation motion of the instrument at the distal end of the sleeve. Preferably, the translation between the proximal end and the distal end is one to one (1:1), i.e. a twist of 20° at the proximal end should lead to a 20° rotation of the instrument tip.

The needle is slidably movable with respect to the protective hull through one or more control wires, which may be actuated via a suitable slide actuator at a proximal end of the instrument. Preferably, the needle is slidable back and forth with respect to a fluid supply passageway which conveys the fluid to the needle for delivery. The fluid supply passageway may be an integral part of the sleeve, or may be a tube statically mounted in the sleeve. The ability to move the needle back and forth while conveying fluid to the needle through a conduit which does not move relatively to the sleeve enables a retractable needle to be provided within a smaller diameter sleeve than a device in which a fluid delivery tube must slide along the length of the sleeve.

The sleeve may comprise a multi lumen tube. The lumens may be formed by inserting an extruded separator element inside a single lumen tube. The extruded separator element may include a U-shaped channel for guiding the coaxial cable and one or more through holes for carrying the fluid feed conduit and control wire(s).

The diameter of the sleeve is preferably less than 2.8 mm to enable it to fit down the instrument channel of an endoscope. The handle for applying torque to the sleeve may be located at the proximal end of the sleeve, near the endoscope controls.

The instrument may include a cap element at the distal end of the sleeve, the cap element covering the electrical joint between the coaxial cable and the first and second conductive elements. The cap element may be formed from a heat shrink material or from potting adhesive. Protecting the joint in this way may prevent arcing from occurring at the electrical joint during use. In particular, the cap element is arranged to seal the distal electrical connections from fluid at the instrument tip. Ingress of fluid to the junction where the co-axial cable is connected to the parallel plate planar transmission line is undesirable, as either the microwave energy may be absorbed, which will lead to heating and the energy not being delivered along the edge of the blade in an efficient manner, or the device will breakdown or flashover due to the lower breakdown voltage. The potting adhesive may comprises a combination of glues, e.g. low viscosity and high viscosity UV curing medically approved glues may be used such as Loctite® 4304 or Loctite® 4305, the low viscosity adhesive being useful for filling gaps, and the low viscosity being useful for wicking the adhesive into very fine potential fluid paths.

The instrument tip may also be arranged to receive microwave frequency energy. The coaxial cable may be arranged to convey a microwave signal separately from or simultaneously with the RF signal. The first and second conductive elements may be arranged on the first dielectric element to act as a near field antenna to radiate microwave frequency energy corresponding to the received microwave signal.

This arrangement may make use of the ability of the instrument to be "seen" differently by the RF signal and microwave signal. For the RF signal, the instrument tip may be modelled as a parallel plate capacitor. The electric field set up by the RF signal between the first and second conductive elements can be substantially contained with the planar body (first dielectric material) by setting the edges of the first and second conductive layers back from the side edges of the planar body. To perform RF cutting, it is desirable for the field to extend outside the planar body. In this invention it is possible to do this be extending the edges of the first and second conductive layers up to the side edge of the planar body in a region designated as an RF cutting portion. The RF field set-up between the two plates of the parallel plate capacitor (or planar transmission line) and coupled into the biological tissue, through making contact with one or more edges of the blade, may create a controlled microplasma and the microplasma may enable or enhance the tissue cutting process.

Meanwhile, for the microwave signal, the instrument tip may be modelled as a parallel plate transmission line with the planar body representing dielectric material separating two conductive plates. The radiation pattern of the microwave frequency EM energy in this case depends on the overall shape of the planar body and the microwave feed structure. In this particular instance, the gap at the proximal end between the co-axial feed line (centre conductor) and the upper conductive layer plays an important role in ensuring that the microwave energy from the source is matched in terms of impedance with the load impedance presented by the tissue. The overall length of the planar transmission line arrangement is also important in terms of matching the impedance (or the energy delivery) of (or from) the coaxial transmission line with (or into) the biological tissue, i.e. the structure may form a quarter wave impedance transformer or a half wavelength resonator. Using known simulation tools, this may be modelled to control from which edges the microwave frequency EM energy is radiated. For example, the instrument tip may be configured to inhibit radiation of the microwave frequency energy from a distal edge of the planar body.

Herein, radiofrequency (RF) may mean a stable fixed frequency in the range 100 kHz to 5 MHz and microwave frequency may mean a stable fixed frequency in the range 300 MHz to 100 GHz. The RF energy should have a frequency high enough to prevent the energy from causing nerve stimulation and low enough to prevent the energy from causing tissue blanching or unnecessary thermal margin or damage to the tissue structure. Preferred frequencies for the RF energy include spot frequency in the range 100 kHz to 1 MHz. Preferred spot frequencies for the microwave energy include 915 MHz, 2.45 GHz, 5.8 GHz, 14.5 GHz, 24 GHz.

BRIEF DESCRIPTION OF THE DRAWINGS

Examples of the invention are discussed below with reference to the accompanying drawings, in which.

DETAILED DESCRIPTION; FURTHER OPTIONS AND PREFERENCES

Figure 1:
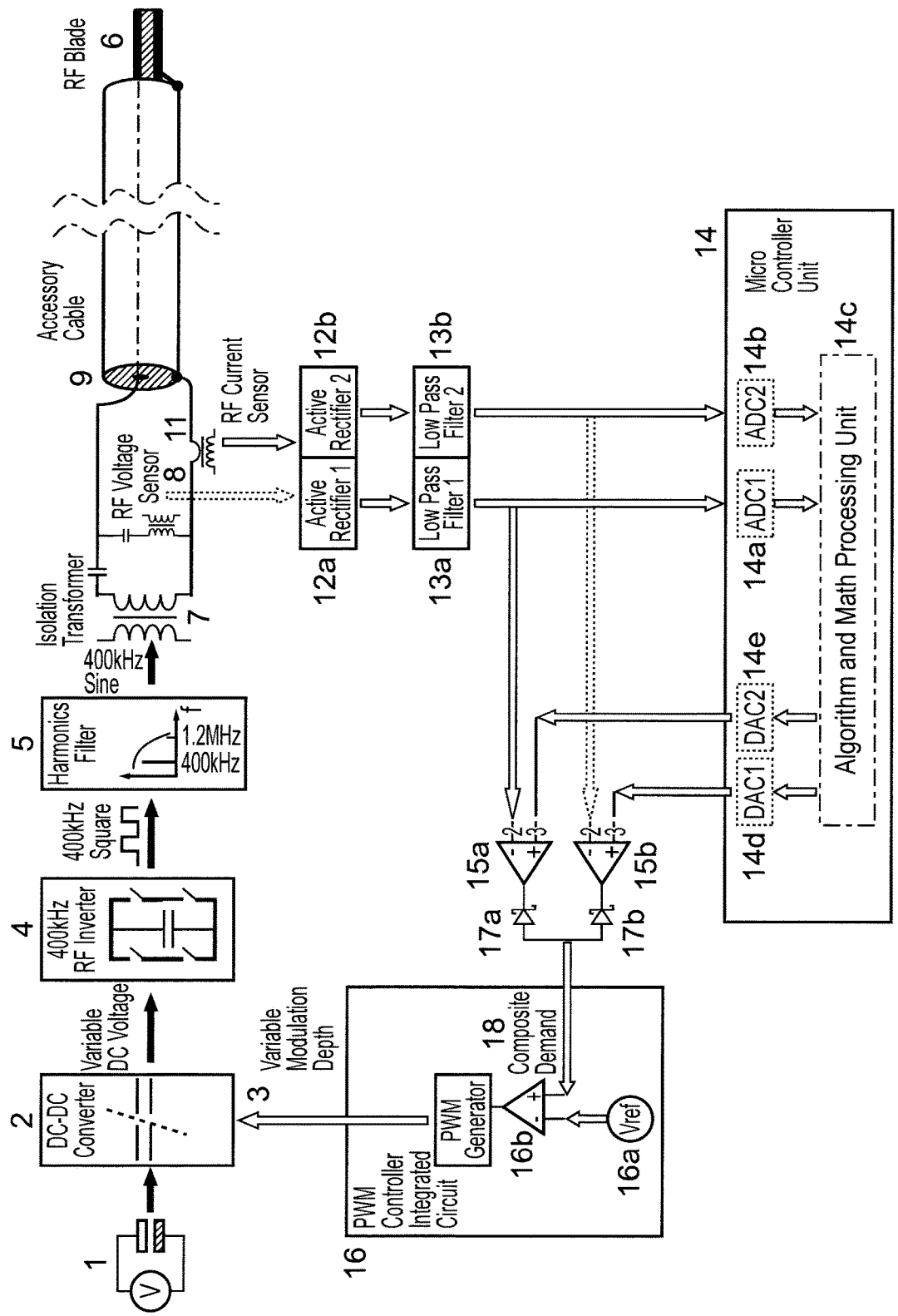
FIG. 1 is a schematic drawing of an electrosurgical apparatus that is an embodiment of the invention.

Earlier electrosurgical systems required the surgeon to determine optimal settings for each surgical accessory (e.g. probe) from instructions for use, training and experience. This far from optimal arrangement was improved with increasing incidence of designs allowing for pre-selection by the generator of default initial treatment settings, based on the accessory type attached and the treatment procedure to be conducted. Pre-selection might be as a result of manual selection of the surgical accessory from a user interface menu on the generator, or by automatic recognition of the accessory by communication between surgical accessory and electrosurgical generator. Even in such a design, the surgeon could be required to modify the generator settings to achieve optimal settings for a given patient, surgeon technique and surgical procedure. In practice, in the absence of evidence of the effect of each generator setting, and as a result of the lack of knowledge of how to efficiently navigate settings menus, these newer generators generators are predominantly used with default but potentially suboptimal settings for all or part of a procedure.

Embodiments of the present invention provide an automatic adaptation of the generator output to suit the detected surgical conditions without requiring operator intervention, thereby freeing the clinician to focus on other pressing aspects of patient treatment.

A problem particular to the endoscopic application of such a device, arises partly as a constraint of restricted size, and therefore the thermal mass of the RF blade. It is typical for the endoscope lumen through which the blade must pass to be of the order of 2.8 mm diameter. This limits the design scope to mask off parts of the RF blade that are exposed to tissue but which do not add to dissection performance. These constraints are distinct from a similar RF dissection device in a laparoscopic environment, where the norm is for a 5 mm diameter port lumen.

In endoscopic procedures the clinician is typically addressing pathologies on the inner wall of the alimentary canal, and a subset of these procedures involve dissection within the heterogeneous layers of these walls. Such procedures are collectively known as Endoscopic Mucosal Resection (EMR).

A further particular distinction of the EMR application is that in a first part of the procedure the blade may be used to dissect with superficial contact to tissue, just beyond the margin of a tumour that has not invaded the outer layers of the digestive lumen; and in second part of the procedure the same blade is required to dissect under the tumour and achieve separation from the muscle layers. In this second part of the procedure, a significant proportion of RF blade may be in intimate contact with the flap tissue. For ease of separation of tissue strata, the specimen flap being resected may be distended and conveniently tumesced by injection with such as saline, hyaluronic acid or a solution of succinylated gelatine. The term Endoscopic Submucosal Dissection (ESD) is the term used for the development of EMR procedures augmented by the means of injected fluids, and is distinct in scope from EMR as it allows for en-bloc dissection of 2 cm and greater diameter mucosal tissue specimens.

From a surgical operator's point of view, it is desirable for the RF cutting instrument to provide a minimally interrupted cutting performance, which in the first part of the procedure is possible as there is only limited contact between tissue and instrument tip. However, during the second part of the procedure the specimen flap cannot easily be separated from the instrument tip and the result is a large contact areas between the active parts of the instrument tip and the tissue, despite the desire being to only have contact at the periphery of the instrument tip for dissection purposes. In addition where there has been pooling of injected fluids under the specimen flap there is a requirement for the blade to be able to achieve cutting while immersed in fluid. These fluids may be electrically conductive which affects the efficiency of plasma generation, and will be more thermally conductive which tends to thermally quench the plasma cutting edges of the RF instrument tip. In this latter case the RF waveform must deliver much more power to initiate and sustain the cutting plasma.

Towards the end of the procedure, the clinician has typically advanced to the point of almost having completely detached the tumour specimen from the lumen wall. At this stage it is likely that the blood supply to the specimen will have been stemmed and this tends to reduce the ohmic conductivity of the remaining tissue, as blood is electrically conductive at RF frequencies. In addition where the fluids injected to tumesce the specimen and its margins are of a non-polar nature, the result can be that the tissues in electrical contact with the RF blade at the final part of dissection are much higher in impedance, which makes the focussing of heat around one part of the RF blade more difficult. Without such a focus, the fluids in the tissue local to the blade will be more difficult to locally desiccate and, thus it is more difficult to create the conditions for initiating a cutting plasma. To create the same level of ($V^2/R$) heating in the volume that will be become a cutting plasma, the applied voltage must be increased to counteract the increase in circuit impedance.

To address this issue the waveform is further optimised by periodically having a short duration increase in voltage amplitude. The rationale for the short duration is that this minimises the average dielectric heating in the insulation layers of the surgical accessory or on any eschar built up across said insulation; but from the point of view of impact on plasma generation, it may be almost as effective as a waveform of a continuously higher voltage amplitude. The reason for this is that, counterintuitively, a plasma volume such as deployed for RF cutting of tissue, has a much higher impedance than tissue. As a plasma is generated therefore, the voltage that is dropped across the portion of tissue which does not form part of the plasma, falls. The voltage applied by the RF cutting blade is predominantly across the plasma, and one could expect the current delivered by the surgical accessory to the tissue to fall for the same amount of delivered power. In fact if the voltage applied is dropped to that just required to sustain local power density maintaining the plasma, the power level applied to the aggregate medium of tissue and plasma can often fall. This effect described above may be enhanced by the presence of a small amount of conductive fluid at the treatment region. The instrument may therefore be adapted to deliver one or more droplets of conductive fluid (e.g. saline) to the distal end thereof. Where the instrument includes a retractable needle, the conductive fluid could be delivered from the needle in its retractable position, whereby it will flow toward the treatment region at the distal end of the probe.

Thus, the present invention is built on the premise that within an endoscopic environment for RF tissue cutting, it is beneficial to provide a RF waveform in which transient higher power levels can be delivered by the probe and transient higher voltage levels can be delivered to the probe.

As mentioned above tissue may adhere to the instrument tip and in particular adhere across the insulation that separates the two electrical poles of the instrument tip structure. As this tissue ohmically heats up from the applied RF voltage the hydrocarbons dissociate and the carbon residues are an increasingly conductive resistance in shunt with the patient tissue being treated and so increasing amounts of power are required to sustain cutting performance. This can become a runaway process culminating in premature blade failure from loss of metallisation and from temperature excursion of the blade insulation. This process can be minimised by periodically interrupting the applied RF waveform. The plasma edge of the blade is rapidly quenched during the OFF portions of the RF waveform as liquids re-establish physical contact, and this tend to be self-cleaning and reduces the average temperature of the instrument, thereby extending the useful life of the instrument.

Thus, in addition to a desire to have transiently higher power levels and transiently higher voltage levels, the waveform preferably also has periodic OFF period interruptions.

According to one embodiment of the invention, the present invention provides an electrosurgical generator arranged to deliver an adaptive RF cutting waveform with the following characteristics.

Firstly, the waveform is regularly pulsed in nature. In this embodiment the period of each pulse is 140 ms, although the invention need not be restricted to this. The maximum ON time of each pulse is restricted to 100 ms. This guarantees a minimum OFF portion for each pulse (having a duration of 40 ms in this embodiment) in which the instrument tip to be quenched and under voltage limit impedances reduces the dissipation in debris adhered to the blade to 70% of that for an uninterrupted waveform.

Secondly, each pulse has a peak power limit that is much greater than the average power for the pulse. In this embodiment the average power level is limited to 30 W, although the clinician may elect to usefully adjust it between 20 W and 35 W. However, the RF signal generator may be capable of generating RF waveform with a cycle average power level of up to 100 W. Thus, to meet the average power level restriction for the pulse, the ON portion of each 140 ms pulse can be curtailed if the energy delivered per pulse is computed to exceed allowed average power level multiplied the pulse period (e.g. 30 W×0.14 s=4.2 J)

Thirdly, the leading edge of each ON portion of a pulse has a higher cut initiation voltage limit followed by a lower cut sustain voltage limit, which is maintained to the end of the ON portion of that pulse. In this embodiment this cut initiation voltage limit is set for up to 20 ms from the leading edge of the ON portion of the pulse, and has an amplitude of 305 Vrms. The cut sustain voltage limit has an amplitude of 290 Vrms.

Figure 2:
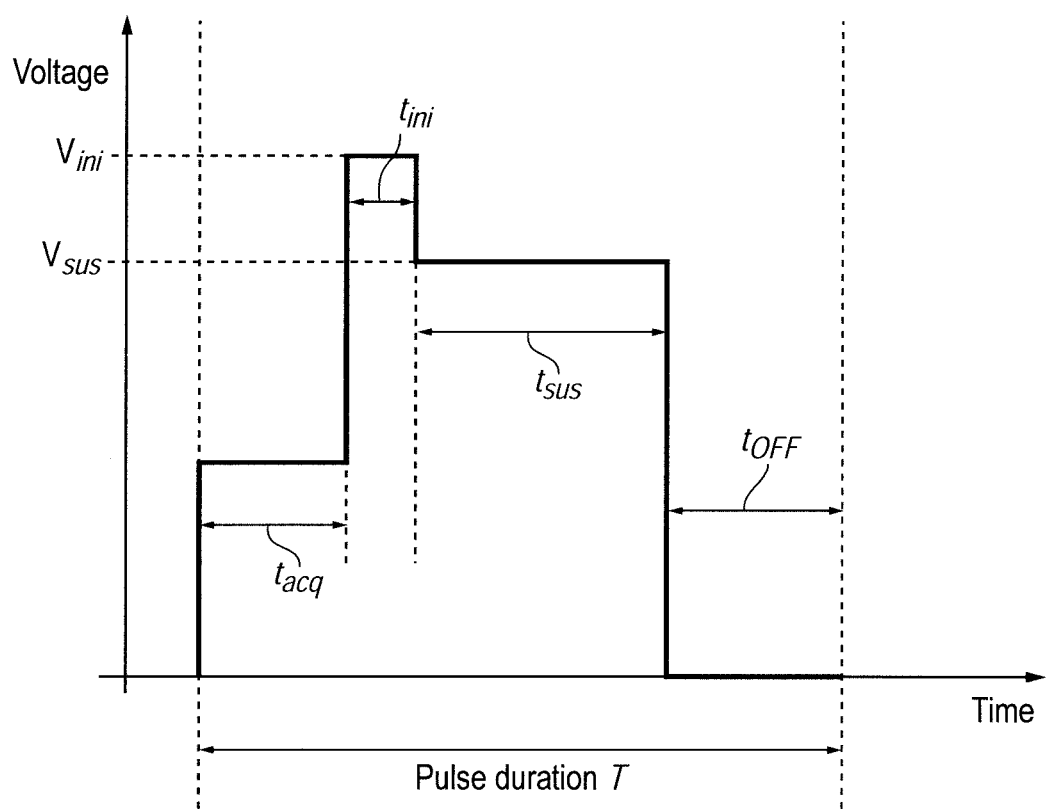
FIG. 2 is a schematic graph showing the profile of an RF signal pulse used in an embodiment of the invention.

The above characteristics are illustrated in FIG. 2, which is a schematic graph showing how the voltage of RF energy delivered by the RF signal generator varies within individual RF signal pulses. The duration (period) T of each pulse is the same, e.g. 140 ms in this embodiment. The voltage of the RF energy delivered by the RF signal generator is controlled via a control signal from a microprocessor controller, as described below. The control signal controls three parameters in order to limit or otherwise control the profile of each RF signal pulse. The three parameters are (i) a limit for current passing through the biological tissue, (ii) a limit for the voltage applied across the poles of the instrument tip, and (iii) the power delivered to the tissue.

Figure 3:
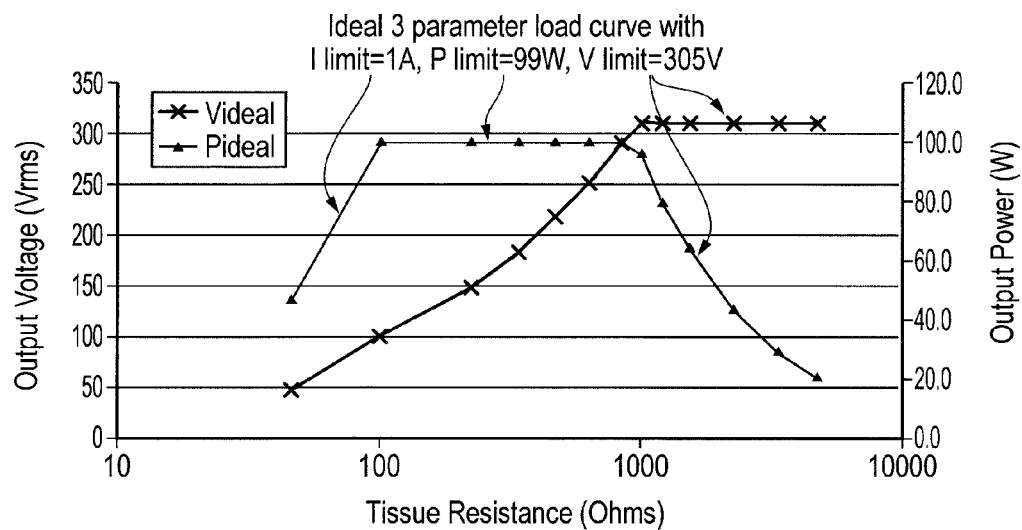
FIG. 3 is a graph showing an ideal three parameter load curve that may result from implementation of the control method of the present invention.
Figure 4:
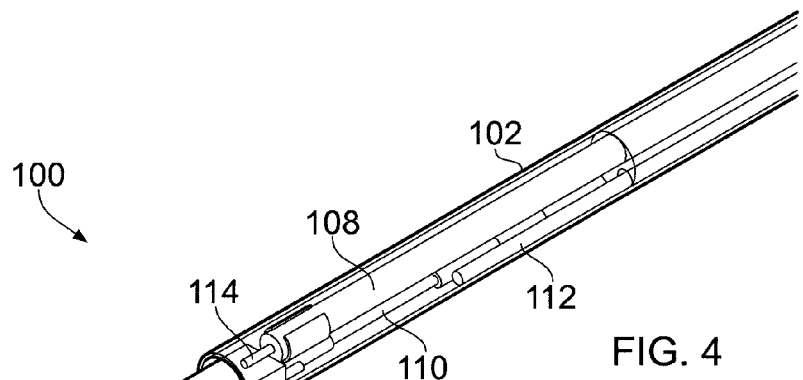
FIG. 4 is a partly transparent perspective view of an electrosurgical instrument that may be used as a probe in the present invention.

The rationale for using these parameters is as follows. Firstly, at low tissue impedances, the ceiling current limits the local dissipation or current density in any one series element in the path through tissue via the probe and feed structure. Secondly, at high impedances the ceiling voltage prevents overstress of the probe's insulation while being sufficiently high to sustain the desired intensity of RF cutting. Thirdly, at moderate tissue impedances, the ceiling power limits the macroscopic rate of energy delivery to the tissue, such as for ensuring required temperatures can be met for cutting. An ideal load curve showing the balance between this limits is depicted in FIG. 3.

Of these three parameters, current under low tissue impedance conditions, and voltage at high tissue impedance conditions can be readily measured at the generator at the output of the RF synthesis stage, and used to regulate waveform amplitude. Power is more challenging to derive directly across a range of tissue impedances due to the impact on measurement of parasitic impedances of the accessory cable.

To provide the required power limit control at moderate tissue impedances, the invention uses current and voltage measurements at the output of the RF synthesis circuit, and a known RF synthesis frequency, and a known lumped shunt capacitance associated with stray capacitances and feed structure (i.e. coaxial cable) capacitance to dynamically compute the tissue resistance. From this information the current limit at the output of the generator can also be dynamically adjusted to that required to provide the required dissipation in the tissue resistance. An advantage of having at a persistent computation of the tissue current and resistance is that the controller is able to also maintain a computation of the actual energy delivery over a given period of time, despite any temporal variations in the generator output power.

When the envelope of the applied cut waveforms is pulsed, the rate of power control needs to be short compared to the mark (ON) time of the pulse, so as to have control over most of the mark time. The microprocessor controller thus runs a control loop routine to set the state of the control signal. The pulse duration T may be set as a multiple of the control loop routine period. For example, the control loop routine period may be 10 ms, but is preferably 100 μs or less.

The control loop routine functions to dynamically adjust the current limit between a minimum value corresponding to the expected current with no tissue connection to the probe (i.e. $V_{limit}/X_c$) and a maximum value corresponding to the limit set for low tissue impedances.

In a practical embodiment, the RF signal generator, which may be a 400 kHz source, is coupled to the probe (RF cutting instrument) by a feed structure that can be treated as a combination of transmission lines of short electrical length (i.e. physical length/wavelength<<0.01), and accordingly a lumped equivalent circuit approximates with sufficient accuracy to the combination of distributed series inductance and shunt capacitance elements.

In an example system embodiment with a coaxial feed cable length between generator fascia and probe of 3.8 m, the lumped shunt capacitive impedance $X_c$ is measured as $-j800\Omega$ or about 500 pF. In practice this may be comprised of stray capacitances in shunt plus the predictable lumped shunt capacitance of the surgical accessory cables.

In this embodiment the coaxial cable has a characteristic impedance of 50Ω which allows a ceiling value to be estimated for the lumped series inductor, at 1.2 µH or about j3Ω. The impact of the this ignored lumped series element on the calculation of the power delivered to tissue is only significant at low tissue impedances. Low tissue impedance is only a transient condition at the onset of cut waveform application or is a tissue condition that will not involve RF cutting if sustained and as such this is not a condition that is particularly pertinent to a cutting waveform. Further, at such a low tissue impedances, the power control limit will be overridden by the fixed output current limit control.

Figure 8:
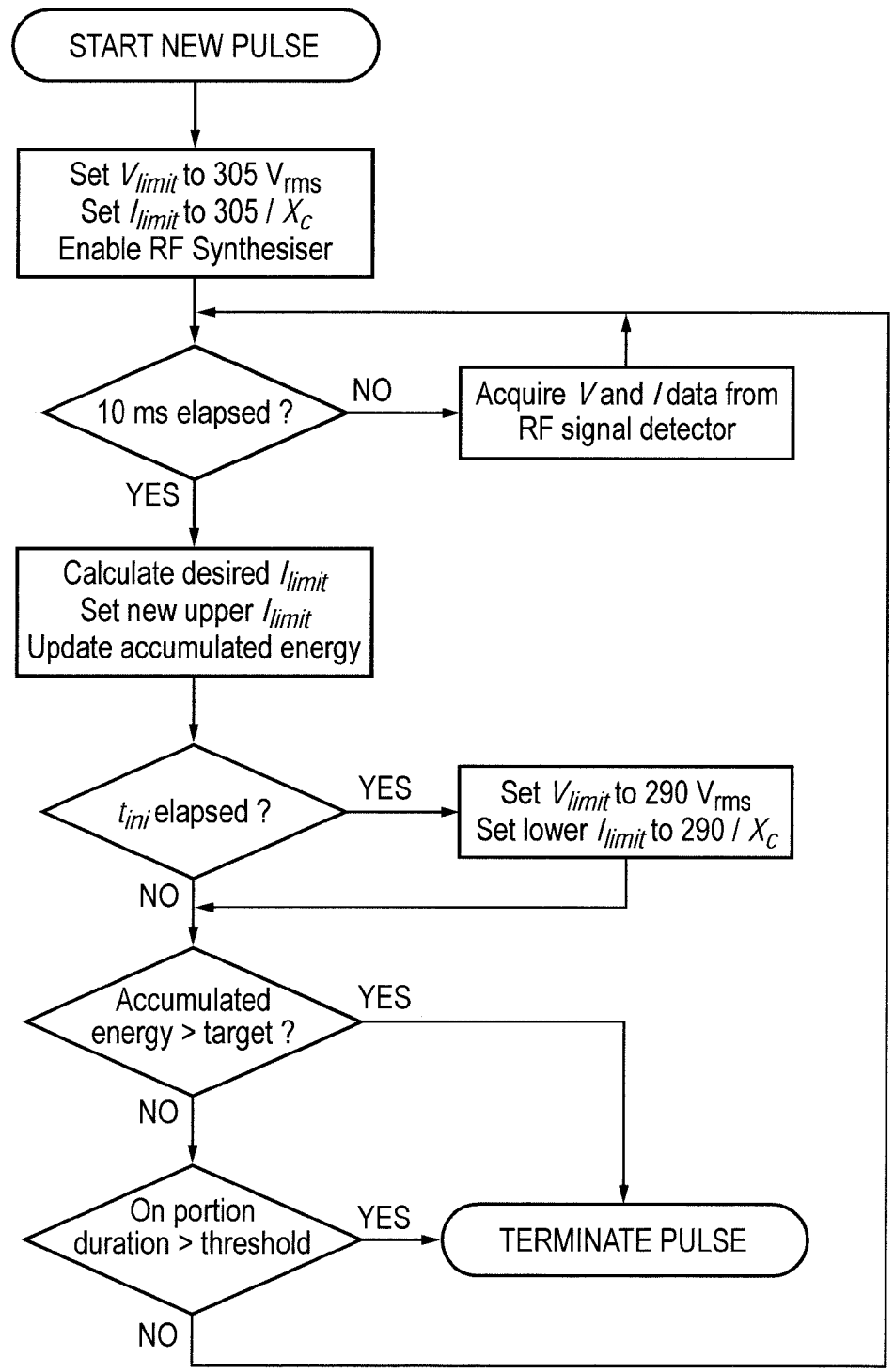
FIG. 8 is a flow diagram illustrating a control method for accurately controlling the power delivered at a probe tip, which is an embodiment of the invention.

As shown in FIG. 8, at the start of each RF signal pulse period, the control loop routine may be set to output a first state for data acquisition before initiating the cutting action. The first state corresponds to a short information acquisition portion $t_{acq}$ to detect the impedance of the load at the distal end of the probe. During this portion, the initial current limit for the output of the RF synthesis stage, in the absence of any valid tissue impedance data, is that corresponding to the expected current with no tissue connection to the probe. The first state corresponds to a data acquisition portion of the pulse, where the cut initiation voltage limit $V_{limit}$ is set high, e.g. 305 Vrms, and the current limit $I_{limit}$ is set to $V_{limit}/X_c$, where $X_c$ is the impedance of the feed cable. This is a conservative setting that ensures that irrespective of the tissue impedance, the load curve boundary is not exceeded. In an alternative (preferred) approach, the current limit $I_{limit}$ is set to the value corresponding to the expected current at the generator where the load curve voltage limit boundary intersects that power limit boundary. In this case, target current may be calculated as $I_t=P_{pk}V_{limit}$, where $P_{pk}$ is the intra pulse power limit and $V_{limit}$ is the set voltage limit. The current limit $I_{limit}$ can be calculated as $I_{limit}=\sqrt{(V_{limit}/X_c)^2+I_t^2}$, where $V_{limit}$ is the set voltage limit, $I_t$ is the target current, and $X_c$ represents a lumped shunt capacitance associated with the RF channel.

As the RF energy is delivered to the probe, the control loop routine is arranged to acquire (e.g. from a plurality of data acquisition points) detected voltage and current information from the RF signal detector. Periodically, e.g. every 10 ms, the acquired information may be used to calculate a value for the resistance at the instrument tip using a value for the lumped element shunt capacitance mentioned above, e.g. using the formula $$R_t = \sqrt{\frac{1}{((I_{out}/V_{out})^2 - 1/X_c^2)}}.$$

The calculated tissue resistance is used in turn to calculate a desired tissue current, e.g. using the formula $$I_t=\sqrt{(p_{set}/R_t)}$$

and hence to dynamically update the current limit to constrain the current at the instrument tip to a desired range over the remainder of the ON portion of the pulse, i.e. the cut initiation portion and cut sustain portion. The current limit may be set using the formula $$I_{limit}=\sqrt{(V_{out}/X_c)^2+I_t^2}.$$

Figure 9:
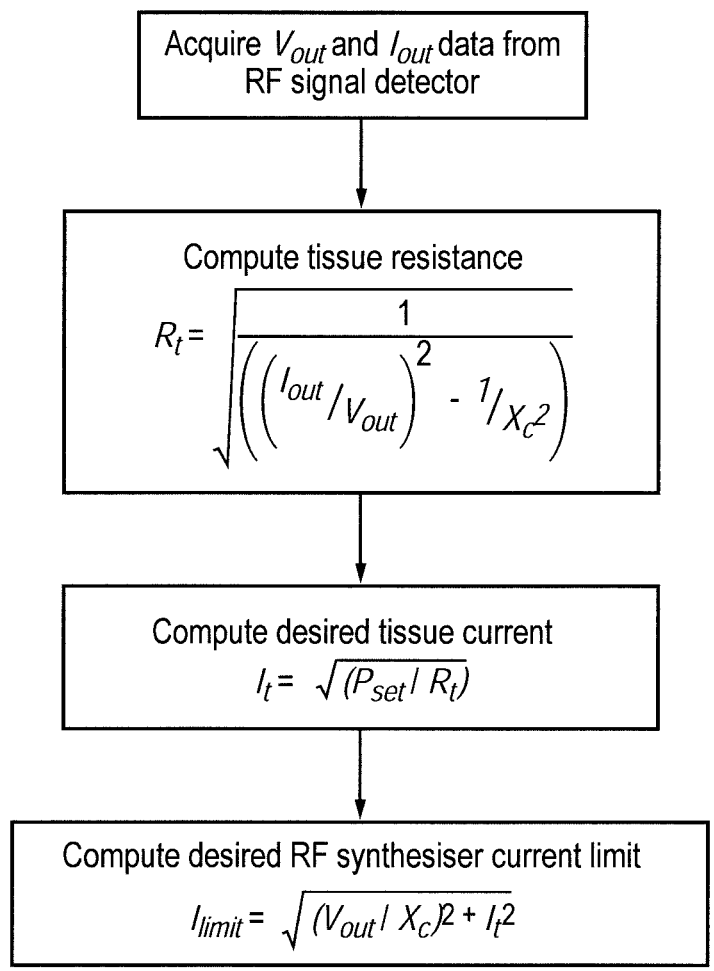
FIG. 9 is a flow diagram is a flow diagram illustrating how the current limit is calculated in the control method of FIG. 8.

A result of updating the current limit in this way will be to limit the delivered power to $P_{set}$ over the range of tissue impedances defined in the load curve. FIG. 9 illustrates this sub-routine of the control loop in more detail.

In this embodiment, after the data acquisition portion, the controller is arranged to output a second state, which corresponds to a cut initiation portion of the pulse. In this embodiment, the cut initiation portion has a set voltage limit $V_{ini}$ that is the same as the data acquisition portion, i.e. 305 Vrms. The control loop routine may be programmed to maintain the cut initiation voltage limit for a predetermined length of time $t_{ini}$, which may correspond to a multiple of the control loop routine period.

When the microprocessor controller determines that the predetermined length of time $t_{ini}$ has elapsed, the control loop routine is arranged to output a third state for sustaining the cutting action. The third state corresponds to a cut sustain voltage limit $V_{sus}$ for the pulse, which is set to a lower value than the cut initiation voltage limit, e.g. 5-10% less than $V_{ini}$, e.g. 290 Vrms.

The control loop routine may monitor the accumulated energy delivered by each pulse. The accumulated energy is determined by using the voltage and current information from the RF signal detector obtained in each control loop routine period in order to calculate an amount of energy delivered during that control loop period. The accumulated energy over N measurements (i.e. data acquisition points) may be expressed as $\Sigma_{n=1}^{N}V_n I_n \tau$, where $V_n$ is the measured voltage of the nth data acquisition point, $I_n$ is the measured current of the nth data acquisition point, and $\tau$ is the duration between each data acquisition point.

Using this information, the duration $t_{sus}$ of the cut sustain portion of each pulse can be automatically controlled to ensure that the energy delivered by the pulse as a whole does not exceed a predetermined threshold. If the control loop routine determines that the accumulated energy reaches or exceeds the predetermined threshold, the control loop routine is arranged to output a fourth state for switching off the cutting action. The fourth state thus corresponds to an OFF portion of the pulse. Effectively, the control loop dynamically controls the duty cycle of each pulse to ensure a consistent limit to the delivery of energy across the plurality of pulses. The duration $t_{OFF}$ of the OFF portion therefore varies with changes in the duration $t_{sus}$ of the cut sustain portion in order to maintain a constant total pulse period T.

The control loop may be arranged to limit the duration of the ON portion (i.e. the cut initiation and cut sustain portions) of each pulse to a maximum value. This ensures that the OFF portion is always at least a certain duration, e.g. 40 ms.

The principle of operation of an RF synthesiser stage that is an embodiment of the invention is described below, in relation to FIG. 1.

The primary energy source for the power conversion stages is a fixed DC supply voltage 1, which could be embodied by a commodity mains to DC voltage switch mode power supply. This is cascaded by a DC to DC voltage converter 2 able to regulate its output voltage continuously in response to a pulse width modulation signal 3 input to the DC to DC converter 2.

The variable DC output voltage of the DC to DC converter 2 is then power-inverted by a 400 kHz RF Inverter 4 to create a 50% duty cycle, square, 400 kHz waveform, that varies in direct relationship to the DC voltage output from the preceding DC to DC converter stage 2. A bridge arrangement of transistors is particularly advantageous in minimising waveform asymmetry from one half cycle to the next, and in turn results in near zero even order harmonics Accordingly this square, 400 kHz waveform is comprised of nth order Fourier components including a primary sine wave at 400 kHz and odd harmonics with amplitude decreasing as reciprocal of the harmonic order. (i.e. 1, ⅓, ⅕, 1/7 . . . ).

The transient response of the output envelope of 400 kHz waveform in response to step changes in demand, is optimised by minimising the energy reservoir storage in the output of the DC to DC converter 2. To assist with this objective, the transistor switching of the DC to DC converter 2 is synchronised to that of the RF Inverter 4 and is operated at as close to the RF Inverter 4 frequency as possible. Note that in general terms the switching loss constraints on the RF Inverter 4 are less than those for the DC to DC converter 2 as the former only operates at one duty cycle, allowing the switching losses to be minimised. In this embodiment, the DC to DC converter stage is operated at 200 kHz synchronous to the 400 kHz RF Inverter 4.

The harmonic content in the output of the RF Inverter 4 is further reduced by the Harmonics Filter 5 which is implemented by a combination of a series band pass LC filter and a shunt LC trap filter. This combination allows for harmonic content reduction for low and high impedances presented across the poles of the RF blade 6, and also for intermediate impedances.

It is a requirement of internationally recognised medical device standards for electrosurgery systems that the patient must be subjected to minimal low impedance connection to circuits, other than that those directly intended to connect to the patient. By example, no more than 1% of the power available to treat the patient on a bipolar system should be dissipated by connection to the local ground potential. The Isolation Transformer 7 stage is therefore ubiquitous, and in this embodiment also operates as a 'gearbox' to match the higher voltages (of circa 300 Vrms) needed for RF plasma generation to the more convenient lower synthesis voltages (of circa 110 Vrms for the fundamental Fourier component output from the RF Inverter 4).

A further prerequisite of the device standards is that connections to the patient should be coupled through capacitors. These prevent net DC charge flowing though the patient tissue in response to the application of an AC waveform. Such a situation can arise should the load become non-linear with polarity. The plasma and arc loads are known to result in a partial rectification of applied currents. Both the output of the Isolation Transformer 7 and the input to an RF Voltage Sensor 8 transformer are coupled to the generator RF output via series capacitors.

The RF current passing in shunt from pole to pole of the Accessory Cable 9, plus that current passing out through the RF Blade 6 to the tissue is sensed by an RF Current Sensor 11.

The signals from the RF Current Sensor 11 and the RF Voltage Sensor 8 are processed in duplicate circuits as follows. In a first step the AC RF signal is rectified in Active Rectifiers 12a, 12b with minimal distortion using an operational amplifier arrangement similar to that published by Analog Devices Incorporated. Precision resistors are used to ensure that half-cycle to half-cycle matching is achieved. It is possible to obtain resistor packs with 0.05% match from resistor to resistor which are ideal for this application.

The full wave rectified signals are then filtered in Low Pass Filters 13a, 13b to remove RF components, which result in two signals, respectively representative of the envelope of amplitudes of the RF voltage and RF current. Due to the low harmonic distortion in the RF current and RF voltage fed into the RF Cable 9, these average signal levels are representative of both the Root Mean Square (rms) and peak values, assuming appropriate scaling factors (Vpk×2/π=Vaverage, and Vpk/√2=Vrms).

The signal outputs of the Low Pass Filters (13a, 13b) are fed to both (i) the Analogue to Digital Converter (ADC) 14a, 14b inputs of the Micro-Controller Unit (MCU) 14; and (ii) first stage Error Amplifiers 15a, 15b for the PWM Controller 16 of the DC to DC converter 2.

Given prior knowledge of the reactive impedance Xc of the Accessory Cable 9, and dynamically updated signals proportional to the rms values of the RF current and voltage fed to the Accessory Cable 9, the Algorithms and Maths Processing Unit 14c is able to dynamically calculate the rms current passing through tissue from connection with the RF Blade 6, at a given applied RF voltage. The load impedance is computed by the Algorithms and Maths Processing Unit 14c of the MCU 14, which allows the deduction of the required current at the RF Blade 6 based on the published load curve for the attached surgical accessory (see FIG. 3).

The required input current Accessory Cable 9 to achieve the desired RF Blade 6 current is dynamically computed and loaded into the Digital to Analogue Converter (DAC) channel for current limit 14d. During treatment the DAC channel for voltage limit 14e is statically set at the ceiling value allowed by the selected accessory load curve. It may be advantageous to gradually ramp up the DAC channel for voltage limit 14e under transient conditions, such as at the leading edge of a pulse or in response to a detected abnormal tissue condition. These do not form part of the control loop design described herein.

First stage Error Amplifiers 15a, 15b compare the average output RF current and RF voltage against the limit values set by the DAC channels 14d, 14e, and the outputs of these amplifiers are diode ORed together by diodes 17a, 17b. Thus the PWM Controller 16 is presented with a Composite Demand signal 18 that only increases when both RF current and RF voltage levels are below the limit levels set by the MCU DACs 14d, 14e.

Some Controller ICs are oriented to provide either a greater depth of modulation in response to an increasing input (demand) signal; whereas others provide a lesser depth of modulation in response to an increasing input (output intensity) signal. In this embodiment, the PWM Controller 16 has its internal voltage reference 16a linked to the negative input of the internal error amplifier 16b so that an increasing Composite Demand signal 18 increases the depth of modulation applied to the input 3 of the DC to DC converter 2.

In summary therefore the output of the DC to DC converter 2 only increases when both RF current and RF voltage levels are below the limit levels set by the MCU DACs. In general one parameter is exclusively in control as a function of RF tissue impedance, the exception being the intersection of the constant power boundary and constant voltage boundary on the published load curve.

An example of an electrosurgical instrument 100 that can be used as a probe in an embodiment of the invention is now described with reference to FIGS. 4 to 7. The instrument comprises a sleeve 102 having an instrument tip 104 connected at its distal end. The sleeve 102 is made from a flexible polymer material (e.g. Pebax®) having axially-extending braids (e.g. of metal) encapsulating within it. This arrangement forms a torque stable system. The braids may not extend right up to the distal end of the sleeve, thus introducing a safe distance (e.g. of no less than 1 mm as measured along the longitudinal axis between the end of the braid and the proximal edge of the instrument tip in order to avoid any risk of heating of the braid as a result of capacitive conductance during use of microwave energy. A sleeve without braid may extend across this safe distance gap. This arrangement also prevents the two plates of the planar transmission line or the two conductors in the co-axial transmission line from becoming shorted or connected together. The braid structure enables torque applied to the proximal end of the sleeve to be accurately transformed into rotational movement of the instrument tip 104. For convenience, the sleeve 102 is shown as transparent in the drawings to permit illustration of its internal components. In practical embodiments, the sleeve may be opaque.

The instrument tip 104 comprises a dielectric block 106 that has layers of metallisation 105, 107 on its upper and lower surfaces. The layers of metallisation correspond to the first and second conductive elements of the invention. The layers of metallisation are separated by the thickness of the dielectric block 106 to form a bipolar radiating spatula structure, similar to that disclosed in GB 2 472 972.

The layers of metallisation may be formed from high melting point conductors, e.g. W or Ti. In such an arrangement, lower melting point conductors may be deposited around the regions where the coaxial cable connects to the parallel plate planar transmission line to facilitate soldering the coaxial arrangement to the planar transmission line. The lower melting point conductors may be silver (Ag) or gold (Au).

Figure 5:
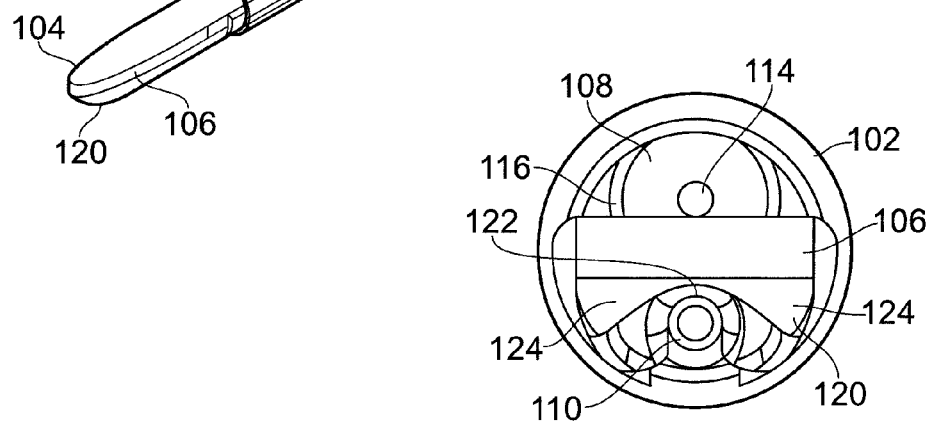
FIG. 5 is a front view of the instrument of FIG. 4.
Figure 6:
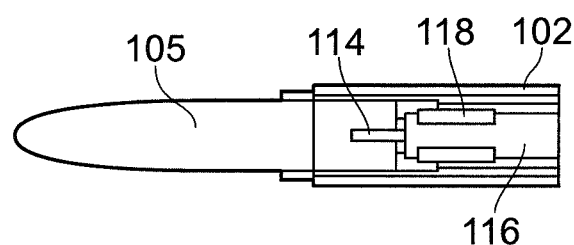
FIG. 6 is a top view of the instrument of FIG. 4.
Figure 7:
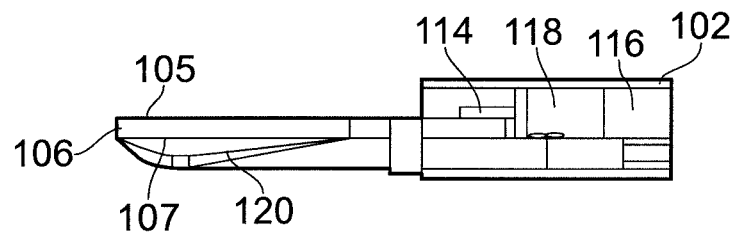
FIG. 7 is a side view of the instrument of FIG. 4.

As seen most clearly in FIG. 5, the distal end of the dielectric block is formed in a curved, e.g. parabolic, shape. This shape is preferred so that the instrument does not present sharp corners at its outer edges, and to enable use in multiple directions of travel. Such sharp corners can be undesirable when the instrument is used in environments with delicate tissue structures, such as the gastrointestinal tract, where the bowel wall is very thin.

The sleeve 102 defines a lumen which carries a flexible coaxial feed cable 108 and a fluid delivery structure. In this arrangement, the fluid delivery structure includes a passageway formed by space in the lumen around the flexible feed cable 108 and a retractable needle 110. The sleeve 102 carries a control wire 112 for both deploying and retracting the needle 110.

The inner conductor 114 of the coaxial feed cable 108 protrudes from the distal end of the coaxial feed cable 108 and is electrically bonded (e.g. using solder) to the upper layer 105 of metallisation (first conductive element). The outer conductor of the coaxial cable 116 is electrically coupled to the lower layer of metallisation 107 (second conductive element) by a braid termination 118. The braid termination 118 comprises a tubular part that is electrically bonded to the outer conductor and a distally extending plate part 109 that fits under the dielectric block 106 and is electrically connected to the lower layer 107 of metallisation.

In this arrangement, a shaped piece of dielectric material 120 is attached to the lower surface of the dielectric block 106. It may be secured to the lower layer 107 of metallisation. The underside of the shaped piece of dielectric material 120 has a configuration particularly suited for use in procedures performed in the gastrointestinal tract. In the longitudinal direction, the shaped piece of dielectric material 120 comprises a distal part which gradually tapers (e.g. in a curved manner) towards the dielectric block 106. This part of the instrument is in closest proximity to the tissue being treated in use, e.g. the bowel wall, the wall of the oesophagus, the portal vein, or the pancreatic duct. By presenting a curved surface in this way, unwanted perforation of the bowel wall or the wall of the oesophagus or damage to the portal vein or the pancreatic duct can be avoided.

As can be seen most clearly in FIG. 5, the undersurface of the shaped piece of dielectric material 120 has a longitudinally extending recessed channel 122. The recessed channel defines an access path for the retractable needle 110. The recessed nature of the channel means that the access path is flanked one both sides by longitudinally extending ridges 124 of the shaped piece of dielectric material.

The dielectric body 106 and the shaped piece of dielectric 120 may be formed in one piece, i.e. as a unitary body. The unitary body may have a planar slot formed (e.g. cut) therein for receiving a conductive material to form the lower layer of metallisation (second conductive element). The thickness of the slot and therefore the lower layer of metallisation may be 0.1 mm or more, but preferably no more than 0.2 mm.

The overall size of the instrument may be such that it is suitable for insertion through the instrument channel of an endoscope. Thus, the outer diameter of the sleeve may be 2.8 mm or less, e.g. 2.7 mm.

The detailed discussion above relates to delivery of RF waveform from the probe. The electrosurgical apparatus is also arranged to deliver microwave frequency energy in the same way as set out in GB 2 486 343. The microwave energy is delivered using a continuous wave profile, and the preferred average power level delivered at the distal end of the probe (i.e. the instrument tip) is 8 W at 5.8 GHz.

The invention claimed is:

1. Electrosurgical apparatus for resection of biological tissue, the apparatus comprising:
    a radiofrequency (RF) signal generator for generating an RF waveform having a first frequency;
    a probe arranged to deliver the RF waveform from a distal end thereof;
    a feed structure for conveying the RF waveform to the probe along an RF channel;
    an RF signal detector for sampling current and voltage on the RF channel and generating therefrom a RF detection signal indicative of the current and the voltage; and
    a controller in communication with the RF signal detector to receive the RF detection signal,
    wherein the RF signal generator is arranged to deliver the RF waveform as a plurality of RF signal pulses, each of the plurality of RF signal pulses having a predetermined power limit and a pulse duration,
    wherein the controller is arranged to:
        monitor, based on the RF detection signal, energy accumulated in the biological tissue during the pulse duration of each of the plurality of RF signal pulses,
        control a profile of each of the plurality of RF signal pulses to keep an average power delivered by that RF signal pulse to the biological tissue over its respective pulse duration below a target value, and
        cause each of the plurality of RF signal pulses to include:
            a cut initiation portion during which the controller sets a cut initiation voltage limit for the respective RF signal pulse, and a cut sustain portion during which the controller sets a cut sustain voltage limit for the respective RF signal pulse, wherein the cut sustain voltage limit is less than the cut initiation voltage limit, and the cut sustain portion follows the cut initiation portion.

2. Electrosurgical apparatus according to claim 1, wherein the controller is arranged to control a duration of an ON portion of each of the plurality of RF signal pulses to keep an average power delivered by that RF signal pulse to the biological tissue over its respective pulse duration below a target value.

3. Electrosurgical apparatus according to claim 1, wherein the controller comprises a digital microprocessor programmed to output an RF control signal for the RF signal generator, wherein the profile of each RF signal pulse is controlled based on a state of the RF control signal.

4. Electrosurgical apparatus according to claim 3, wherein the state of the RF control signal is determined by a control loop, which runs repeatedly throughout the pulse duration of each RF signal pulse.

5. Electrosurgical apparatus according to claim 1, wherein the pulse duration includes an OFF portion in which no power is delivered.

6. Electrosurgical apparatus according to claim 1, wherein the cut initiation portion of each RF signal pulse has a fixed duration.

7. Electrosurgical apparatus according to claim 1, wherein the controller is arranged to control a duration of the cut sustain portion to keep the average power delivered by its respective RF signal pulse to the biological tissue below the target value.

8. Electrosurgical apparatus according to claim 7, wherein the controller is arranged to stop the cut sustain portion if the monitored accumulated energy exceeds a predetermined threshold.

9. Electrosurgical apparatus according to claim 1, wherein the predetermined power limit of each RF signal pulse is more than three times greater than the target value for the average power delivered by that RF signal pulse.

10. Electrosurgical apparatus according to claim 1, wherein the target value for the average power delivered by each RF signal pulse is 35 W or less.

11. Electrosurgical apparatus according to claim 1, wherein the probe has an outer diameter less than 2.8 mm.

12. Electrosurgical apparatus according to claim 1, wherein the probe comprises:

an instrument tip comprising a planar body made of a first dielectric material separating a first conductive element on a first surface thereof from a second conductive element on a second surface thereof, the second surface facing in an opposite direction to the first surface;

a coaxial feed cable comprising an inner conductor, an outer conductor coaxial with the inner conductor and a second dielectric material separating the inner and outer conductors, the coaxial feed cable being connected to the feed structure for conveying the RF waveform to the instrument tip; and a protective hull comprising a third piece of dielectric material mounted to cover an underside of the instrument tip, wherein the inner conductor is electrically connected to the first conductive element and the outer conductor is electrically connected to the second conductive element to enable the instrument tip to receive the RF waveform, wherein the first and second conductive elements are arranged to act as active and return electrodes to emit the RF waveform from a distal side portion of the planar body, and wherein the protective hull has a smoothly contoured convex undersurface facing away from the planar body.

13. Electrosurgical apparatus according to claim 12, wherein an undersurface of the protective hull smoothly tapers at its perimeter to meet the side of the planar body.

14. Electrosurgical apparatus according to claim 12, wherein a thickness of the protective hull decreases towards a distal end of the instrument tip.

15. Electrosurgical apparatus according to claim 12, wherein the first conductive element comprises a first layer of metallisation and the second conductive element comprises a second layer of metallisation, the first layer of metallisation and the second layer of metallisation being formed on opposite surfaces of the first dielectric material, and wherein the separation of the first and second conductive elements at a distal side portion edge of the instrument tip is less than 1 mm.

16. Electrosurgical apparatus according to claim 12, wherein the protective hull is formed from ceramic or biocompatible plastic.

17. Electrosurgical apparatus according to claim 12, wherein the protective hull and the first dielectric material are formed in one piece as a unitary body.

18. Electrosurgical apparatus according to claim 12, wherein the instrument tip has a curved distal edge.

19. Electrosurgical apparatus according to claim 12, wherein the probe includes a fluid feed conduit for conveying fluid to the instrument tip for delivery out of the instrument tip.

20. Electrosurgical apparatus according to claim 19, wherein the fluid feed conduit comprises a sleeve that defines a lumen for transporting fluid to the instrument tip, the sleeve having a body of the instrument tip and the protective hull secured at a distal end thereof, and being arranged to carry a coaxial cable in the lumen.

21. Electrosurgical apparatus according to claim 20, including a fluid delivery mechanism mounted at the distal end of lumen of the sleeve, the fluid delivery mechanism being operable to deliver fluid from the lumen through the protective hull.

22. Electrosurgical apparatus for resection of biological tissue, the apparatus comprising:

a radiofrequency (RF) signal generator for generating an RF waveform having a first frequency;

a probe arranged to deliver the RF waveform from a distal end thereof;

a feed structure for conveying the RF waveform to the probe along an RF channel;

an RF signal detector for sampling current and voltage on the RF channel and generating therefrom a RF detection signal indicative of the current and voltage;

a microwave signal generator for generating microwave frequency energy having a second frequency that is higher than the first frequency, wherein the feed structure comprises an RF channel for connecting the probe to the RF signal generator, and a microwave channel for connecting the probe to the microwave signal generator, and wherein the RF channel and the microwave channel comprise physically separate signal pathways from the RF signal generator and microwave signal generator respectively, to enable the RF waveform and the microwave frequency energy to be selectively delivered simultaneously or separately to the probe; and a controller in communication with the RF signal detector to receive the RF detection signal, wherein the RF signal generator is arranged to deliver the RF waveform as a plurality of RF signal pulses, each of the plurality of RF signal pulses having a predetermined power limit and a pulse duration, wherein the controller is arranged to:
monitor, based on the RF detection signal, energy accumulated in the biological tissue during the pulse duration of each of the plurality of RF signal pulses, and
control a profile of each of the plurality of RF signal pulses to keep an average power delivered by that RF signal pulse to the biological tissue over its respective pulse duration below a target value.

23. Electrosurgical apparatus according to claim 22, including microwave signal detectors for sampling forward and reflected power on the microwave channel, wherein the controller is in communication with the microwave signal detectors to derive a microwave detection signal indicative of the microwave power delivered by the probe, and is arranged to output a microwave control signal for the microwave signal generator, wherein the profile of the microwave frequency energy delivered by the microwave generator is controllable based on a state of the microwave control signal.

24. Electrosurgical apparatus for resection of biological tissue, comprising:
a radiofrequency (RF) signal generator for generating an RF waveform having a first frequency;
a feed structure for conveying the RF waveform to a probe along an RF channel;
the probe arranged to deliver the RF waveform from a distal end thereof, wherein the probe includes:
an instrument tip comprising a planar body made of a first dielectric material separating a first conductive element on a first surface thereof from a second conductive element on a second surface thereof, the second surface facing in an opposite direction to the first surface;
a coaxial feed cable comprising an inner conductor, an outer conductor coaxial with the inner conductor and a second dielectric material separating the inner and outer conductors, the coaxial feed cable being connected to the feed structure for conveying the RF waveform to the instrument tip, wherein the inner conductor is electrically connected to the first conductive element and the outer conductor is electrically connected to the second conductive element to enable the instrument tip to receive the RF waveform, wherein the first and second conductive elements are arranged to act as active and return electrodes to emit the RF waveform from a distal side portion of the planar body;
a protective hull comprising a third piece of dielectric material mounted to cover an underside of the instrument tip, wherein the protective hull has a smoothly contoured convex undersurface facing away from the planar body, wherein the undersurface of the protective hull has a longitudinally extending recessed channel formed therein; and
a fluid feed conduit for conveying fluid to the instrument tip for delivery out of the instrument, and wherein the fluid feed conduit comprises a sleeve that defines a lumen for transporting fluid to the instrument tip, the sleeve having the instrument tip body and protective hull secured at a distal end thereof, and being arranged to carry a coaxial cable in the lumen;
an RF signal detector for sampling current and voltage on the RF channel and generating therefrom a RF detection signal indicative of the current and the voltage;
a fluid delivery mechanism mounted at the distal end of lumen of the sleeve, the fluid delivery mechanism being operable to deliver fluid from the lumen through the protective hull, wherein the fluid delivery mechanism includes a retractable needle mounted beneath the planar body in the recessed channel of the protective hull; and
a controller in communication with the RF signal detector to receive the RF detection signal,
wherein the RF signal generator is arranged to deliver the RF waveform as a plurality of RF signal pulses, each of the plurality of RF signal pulses having a predetermined power limit and a pulse duration,
wherein the controller is arranged to:
monitor, based on the RF detection signal, energy accumulated in the biological tissue during the pulse duration of each of the plurality of RF signal pulses, and
control a profile of each of the plurality of RF signal pulses to keep an average power delivered by that RF signal pulse to the biological tissue over its respective pulse duration below a target value.

25. Electrosurgical apparatus according to claim 24, wherein the retractable needle is movable in a longitudinal direction between a deployed position in which it protrudes beyond the distal end of the instrument tip and a retracted position in which it is set back from the distal end of the instrument tip.

* * * * *